United States Patent [19]

Herschler

[11] 4,296,104
[45] Oct. 20, 1981

[54] THERAPEUTIC DIMETHYL SULFOXIDE COMPOSITION AND METHODS OF USE

[76] Inventor: Robert J. Herschler, 3080 NW. 8th St., Camas, Wash. 98607

[21] Appl. No.: 71,072

[22] Filed: Aug. 30, 1979

[51] Int. Cl.³ .................... A61K 31/10; A61K 31/17; A61K 33/14
[52] U.S. Cl. ................................. 424/153; 424/322; 424/337
[58] Field of Search ........................ 424/322, 153, 337

[56] References Cited

U.S. PATENT DOCUMENTS

| | | | |
|---|---|---|---|
| 3,334,012 | 8/1967 | Herschler | 424/337 |
| 3,361,555 | 1/1968 | Herschler | 71/103 |
| 3,499,961 | 3/1970 | Dobson et al. | 424/68 |
| 3,549,770 | 12/1970 | Herschler | 424/337 |
| 3,549,771 | 12/1970 | Herschler | 424/337 |
| 3,551,554 | 12/1970 | Herschler | 424/7 |
| 3,558,434 | 1/1971 | Herschler | 195/81 |
| 3,711,602 | 1/1973 | Herschler | 424/45 |
| 3,711,606 | 1/1973 | Herschler | 424/45 |
| 3,740,420 | 1/1973 | Herschler | 424/45 |
| 3,743,727 | 7/1973 | Herschler | 424/181 |
| 4,112,946 | 9/1978 | Herschler | 128/253 |
| 4,177,267 | 12/1979 | Herschler | 424/238 |

OTHER PUBLICATIONS

Mallach, 141, Annals New York Academy of Sciences, pp. 457–462.

Primary Examiner—Stanley J. Friedman
Attorney, Agent, or Firm—Blakely, Sokoloff, Taylor & Zafman

[57] ABSTRACT

The use of urea and/or ethanol with pharmaceutical compositions containing DMSO is disclosed. The result is a reduction in the undesirable side-effects normally associated with the application of DMSO compositions, enhancement of the desired physiological effects produced by DMSO compositions, and other benefits. Specific compositions contain DMSO with urea and/or alcohol and may also contain NaCl, KCl and/or acetamide.

The use of DMSO to reduce the mortality rate of fish treated by hyperosmotic delivery is also disclosed.

8 Claims, No Drawings

THERAPEUTIC DIMETHYL SULFOXIDE COMPOSITION AND METHODS OF USE

BACKGROUND OF THE INVENTION

The present invention relates to pharmaceutical compositions containing DMSO for adminstration to human or other animal subjects. More specifically, it relates to new DMSO formulations containing substances which enhance the effectiveness of DMSO, reduce undesirable side-effects sometimes created by the use of DMSO and make DMSO compositions more appealing to users.

Dimethyl sulfoxide (DMSO) is a versatile substance that has numerous pharmaceutical and nonpharmaceutical uses. It is widely used throughout the world for treating humans and other animal subjects.

As Described in U.S. Pat. No. 3,549,770, No. 3,740,420, and No. 3,790,682, incorporated herein by the reference, DMSO is an active agent in relieving the signs and symptoms of numerous body disorders, including accelerating the healing of certain injured body tissues and in relieving the signs and symptoms of anxiety.

U.S. Pat. No. 3,551,554, No. 3,711,606 and No. 3,743,727, incorporated herein by reference, describe how DMSO is effective to enhance tissue penetration of other substances, especially other physiologically active agents. DMSO can thus be added to a variety of pharmaceutical compositions to accelerate assimilation into body tissue. In some instances this means that smaller doses can be administered when DMSO is used.

Yet, despite their many benefits, DMSO compositions are sometimes passed over in favor of other pharmaceutical compositions even in instances where DMSO would be the most effective pharmaceutical agent. This is because many subjects suffer from one or more side-effects when treated with DMSO. In some cases, the side-effects are so pronounced that subject or physician will forego the use of DMSO in favor of a less effective therapeutic agent.

A variety of undesirable side-effects have been observed to result from administration of DMSO. The most frequently occurring are adverse skin reactions, malodorous breath and foul taste.

The adverse reactions caused by DMSO are well documented. At page 356 of the standard reference Contact Dermatitis by Alexander A. Fisher, M.D. (2nd Ed., 1973), dimethyl sulfoxide (DMSO) is listed as a primary urticariogen. Volume 141 of Annals New York Academy of Sciences includes several articles describing the undesirable side-effects attributed to DMSO. These include articles by Goldman, et al. at pages 429, 433–35; Sulzberger, et al. at pages 439–40; Brown at pages 500–501; and several others.

The magnitude of the malodorous breath problem is so large that, in some instances, hospitals have had to isolate wards where DMSO is administered from the central air conditioning system. Skin irritations from topically applied DMSO have been so great that a substantial number of patients refuse treatment.

Another, potentially more serious side-effect is sometimes observed when DMSO is administered intravenously. This is red blood cell lysis. Intravenous administration of DMSO is crucial if the substance is to be used for treating the brain and spinal cord, for cancer therapy or to treat organ hypoxia, heart attack and other internal conditions. Large intravenous doses of DMSO can have a therapeutic effect for such purposes but red blood cell lysis which results from intravenous DMSO administration can be injurious or even fatal to the subject.

Furthermore, it is generally advisable to minimize the dosage of any pharmaceutical substance administered to a human or other animal subject to the smallest effective amount. Although DMSO is one of the most penetrating of pharmaceutical substances and is known to be effective in minute doses, it would be desirable to further reduce the minimum dosage of DMSO needed to achieve a desired physiological effect.

A related problem is observed when fish are treated with hyperosmotic concentrations of a membrane permeability altering agent as discussed in U.S. Pat. No. 4,112,946, incorporated herein by reference. Such agents include urea, NaCl and acetamide.

These substances, with the possible exception of acetamide, are substantially nontoxic when applied externally to mammalian subjects. But, when incorporated in a solution in contact with an epithelial membrane of fish, such substances can be lethal at moderate concentrations (as low as about 3 weight percent).

To optimize delivery of therapeutic agents to fish, solutions containing greater than 3 weight percent of the above listed solutes are required. Fish mortality is thus a substantial barrier to the effective use of hyperosmotic treatments.

SUMMARY OF THE INVENTION

Specific DMSO compositions and methods of application have now been discovered. Use of such compositions expands the acceptability of DMSO by eliminating or reducing undesirable side-effects. And, the new DMSO compositions and methods of use are observed to provide new therapeutic effects and beneficial uses.

More specifically, it is found that when DMSO and urea are both administered to epithelial regions of a human or other animal subject, expected adverse skin reactions, malodorous breath and foul taste are substantially reduced. In most cases they are entirely eliminated.

Furthermore, urea is discovered to potentiate DMSO in certain instances. It appears that a DMSO composition containing urea and/or ethanol is more rapidly absorbed into tissue than are similar compositions containing no urea or ethanol. If the DMSO composition includes another pharmaceutical substance, such other substance is also absorbed more rapidly when urea and/or ethanol are present. The presence of NaCl, KCl and/or acetamide reduces discomfort resulting from topical application of DMSO compositions and appears to further enhance penetration.

It has also been discovered that certain DMSO formulations, which contain urea, are effective in treating diseased finger and toe nails, for softening cuticle to be removed from finger and toe nails, and for softening epidermal thickenings to ease removal.

When DMSO is administered intravenously with ethanol, red blood cell lysis is reduced and continues to decline with repeated administrations.

When DMSO is added to solutions containing urea, NaCl, and/or acetamide, such solutions are less toxic to fish than similar solutions without DMSO.

It is therefore an object of this invention to provide pharmaceutical compositions and methods to allow the application of DMSO to a human or other animal subject without creating adverse skin reactions, malodorous breath or foul taste.

A further object is to provide compositions and methods of application whereby the lysis of red blood cells, resulting from intravenous administration of DMSO, is reduced.

A further object is to provide compositions and methods of treatments for diseases of the fingers and/or toe nails.

Another object is to provide formulations and methods of application to enhance penetration of DMSO and DMSO based pharmaceutical compositions into animal tissue.

An additional object is to provide safe and effective skin softening agents which can be used to soften cuticle for removal from finger and/or toe nails and for softening epidermal thickenings to facilitate removal.

Yet a further object is to provide means for protecting fish from the toxicity of solutions used for hyperosmotic treatment of fish.

These and other objects, advantages and features of the present invention will be apparent from the following detailed description.

DESCRIPTION OF PREFERRED EMBODIMENTS

The side-effects which have long hindered the use of DMSO as a therapeutic agent are quite surprisingly eliminated when urea is administered with formulations containing DMSO. Even small amounts of urea are beneficial in reducing histamine release, burning and itching, localized dermatitis, drying, cracking and blistering of skin, upleasant breath odor, after-taste, headache and nausea in subjects receiving dermally administered DMSO compositions.

Urea is an especially excellent inhibitor of the side-effects, because it is a naturally occurring substance in human and other animal subjects. Urea is substantially non-toxic and animal subjects are quite tolerant to its presence. It thus can be used with almost any pharmaceutical composition containing DMSO, without fear of toxic effects.

The reasons why urea is effective from reducing and eliminating the above listed undesired side-effects is not fully understood. It appears, however, that the urea inhibits or prevents the production of undesirable DMSO metabolites.

In the case of the breath odor problem, it is known that dimethyl sulfide is a minor metabolite of DMSO and that it is expired through the lungs causing malodorous breath and foul taste. Urea possibly prevents the breakdown of DMSO to dimethyl sulfide. Supporting laboratory experiments show that DMSO will decompose to dimethyl sulfide when heated in a test tube. But, when urea is added and the experiment repeated, no dimethyl sulfide is detected.

Similarly, the adverse skin reaction, such as histamine wheal and flare may be the result of an attack by the dimethyl sulfide molecule against mast cells in the subcutaneous layer of skin to which DMSO is applied topically. Urea's blocking of DMSO breakdown to dimethyl sulfide would thus account for the observed antiurticariogenic effectiveness in reducing adverse skin reactions caused by DMSO.

The enhanced penetration of DMSO solutions containing urea is possibly related to the fact that urea has a weight per volume percentage concentration at isotonicity less than that of DMSO and most other pharmaceutical agents so that, at a given weight percent of solute, compositions containing urea in combination with DMSO, have an enhanced penetrating ability. The effect is even greater if the amount of solute is increased by addition of urea to the DMSO composition.

It appears that the only suitable substances for enhancing the penetration of DMSO compositions are substances having a weight per volume percentage concentration at isotonicity less than that of DMSO, but only a few of such substances produce the desired increase in penetration.

Further criteria of substances which enhance DMSO penetration include water solubility at ambient temperatures and a molecular weight no greater than 78. Substances which tend to polymerize are unsuitable. If the substance is to be used with DMSO-urea compositions applied to living animals, it must also be relatively non-toxic to the intended animal subject.

Specific substances of value in promoting penetration are found to include urea, NaCl, KCl, ethanol and acetamide. Of these substances urea is the most effective. It appears to act by "opening" membranes to allow increased penetration.

The fact that urea, NaCl, KCl, acetamide and/or ethanol may be combined to enhance DMSO penetration is important in several respects. Although urea and ethanol reduce or eliminate the side-effects created by the administration of DMSO, some subjects will continue to have at least mild reactions to the administration of DMSO. By administering urea, NaCl, KCl, acetamide and/or ethanol, it should be possible to reduce the amount of DMSO administered as an active therapeutic agent since greater tissue penetration of the applied DMSO can be obtained. The ability to reduce the amount of DMSO administered, without reducing the amount which is absorbed, should further diminish adverse side-effects of the DMSO.

A similar benefit results when urea, NaCl, KCl, acetamide and/or ethanol are added to compositions which contain DMSO as a carrier and penetration enhancer for other pharmaceutical substances such as antineoplastic agents, analgesics, anti-inflammatory agents, anticoagulants, vasodilators, anti-microbial agents, ultra-violet screening agents, diagnostic dyes, diagnostic radiopaque agents, dietary supplements, nutrients, physiologically active steroids and protein modifying agents.

Protein modifying agents include those substances which modify collagen and, possibly, other substances found in connective tissue such as hyaluronic acid, elastin, and fibrinogen. One such protein modifying agent is methylsulfonylmethane (MSM) as described in my simultaneously filed U.S. patent application entitled Preparations Containing Methylsulfonylmethane and Methods of Use and Purification.

DMSO is a known penetration enhancer for chemical agents having a molecular weight less than about 8,000, administered to intact body membranes. It is also found to enhance the penetration of higher molecular weight substances, such as enzymes, that are administered to stressed membranes including membranes that are inflamed, are scarified or have been subjected to severe osmotic stress. In both situations, the inclusion of urea, NaCl, KCl, ethanol and/or acetamide can further assist the penetration of DMSO and the pharmaceutical agent. Increased penetration can improve pharmaceutical effectiveness and, in some instances, make it possible to reduce the dosage administered.

Penetration enhancing substances, such as urea, are particularly useful in DMSO solutions containing diagnostic dyes. In the staining of cells for diagnostic examination, it is desirable to use the least possible amount of dye and other foreign chemicals to minimize alterations in the cells being dyed. the enhanced cell penetration that results from the addition of urea, makes it possible to reduce the amount of dye and DMSO in staining compositions. The urea added has no adverse effect on the structure of cells to be dyed.

An additional benefit discovered is that human subjects treated with the previously described compositions preferred those compositions containing a salt, most notably NaCl, over similar compositions without salt. Subjects interviewed indicated that topically applied DMSO compositions containing salt are more comfortable.

Urea can be administered with DMSO to produce the same physiological effects attributed to DMSO compositions administered without urea. For example, urea can be administered with DMSO to an area of tissue inflammation in an amount effective for relieving signs and symptoms of inflammation, to a subject suffering from pain in an amount effective to relieve pain, to a subject suffering from abnormal muscle contractions in an amount effective to promote muscle relaxation, to a subject suffering from symptoms of vascular insufficiency in the blood and lymph circulatory system in an amount effective to relieve symptoms of vascular insufficiency.

Treatment with effective amounts of DMSO and urea can also relieve signs and symptoms of a burn, can promote healing of a skin graft area following a transplant, and can relieve signs and symptoms of respiratory distress. When DMSO is given with urea to subjects having joints with arthritic signs and symptoms in an amount effective to relieve signs and symptoms of arthritis, to subjects suffering from tissue damage in an amount effective to promote the repair of tissue damage, or to mammalian subjects suffering from signs and symptoms of anxiety in an amount effective to relieve signs and symptoms of anxiety, improvement in subjects' conditions are observed.

It has also been found that certain compositions, containing both DMSO and urea, have medical benefits not produced by compositions containing DMSO or urea alone. As one example, it is found that DMSO, administered with urea, will repair or remove abnormal, dead, or diseased tissue. DMSO-urea compositions can thus be used to treat interstitial cystitis or connective tissue diseases such as progressive systemic sclerosis.

DMSO-urea, compositions can also be administered to benefit diseased finger and/or toe nails of human or other animal subjects. Administering DMSO and urea to the diseased portion of a nail will soften the diseased portion. After several days of treatment, the diseased portion of the nail can be removed painlessly by gentle urging using forceps. In most instances, the undiseased portion of the nail is not adversely affected by treatment with a DMSO-urea composition.

When used to treat diseased or damaged tissue, DMSO-urea compositions are most effective when applied at a temperature above 37° C., preferably as hot as the subject will tolerate. Warm applications are especially beneficial when treating musculoskeletal disorders such as arthritis, sprains, strains, soft tissue injury and the like.

DMSO-urea compositions are also well suited for use with physical therapy techniques, particularly the use of energy such as ultra sound, in treating musculoskeletal disorders.

As illustrated by several examples below, DMSO-urea compositions soften and moisturize the skin of subjects receiving dermal applications. Certain DMSO-urea compositions accordingly make excellent cosmetic skin softening lotions or gels. Also DMSO-urea compositions are excellent as vehicles for other skin treating cosmetic agents. When the phrase "pharmaceutical compositions" is used herein, it thus includes cosmetic preparations.

Urea is known to have some beneficial effect on skin, but in most standard cosmetic compositions it "washes off". When DMSO and urea are used together, skin permeation of each is enhanced so the skin-softening benefits of urea are increased and sustained even after washings.

As will be described below, the use of ethanol with DMSO in intravenous administrations proved to be independently effective in reducing malodorous breath and red blood cell lysis.

Formulations

As with any multi-purpose pharmaceutical composition, some experimentation is necessary to determine the optimum dosage of DMSO and urea to be applied for a particular purpose. For example, when it is a goal to reduce a side-effect produced by the application of DMSO, the amount of urea used should be an amount effective to obtain the desired reduction. Likewise, if the goal is to enhance penetration, the amount of urea or other penetration enhancing substance should be an amount sufficient to enhance penetration.

As described in the prior patents listed above, DMSO compositions for topical application should contain at least 10 weight percent DMSO to have any beneficial effect. Compositions for clinical use should have at least about 40 weight percent DMSO; and for greatest effect, a composition should contain at least about 50 weight percent DMSO. To be effective in reducing DMSO-induced side-effects and/or to enhance the penetration of DMSO compositions, urea should be present in a weight ratio to DMSO of greater than 1:99. Most significant results are achieved when the weight ratio of urea to DMSO is greater than 1:9. Normally, DMSO-urea compositions should contain no more than about 60 weight percent urea since larger concentrations could only be obtained at the cost of reduced effectiveness due to diminished DMSO amounts.

In special circumstances the desired DMSO concentration for a pharmaceutical composition might be substantially below 10 weight percent or above 50 weight percent. The above urea ratios will still apply in such circumstances. For example, if a low concentration (3 to 4 weight percent) DMSO composition is prepared for application to the eye, a suitable urea amount would be one weight percent.

Compositions containing one weight percent or less of DMSO are effective for treating membranes that have been stressed, e.g. membranes that are inflamed, are scarified or have been submitted to severe osmotic stress. In such instances, the abovestated DMSO-urea ratios would still apply.

Pharmaceutical compositions for treating the skin, oral cavity and rectal epithelium may contain DMSO and urea as their sole components. In any such composition, the weight ratio of DMSO to urea should not be less than about 100:35. Even at this ratio, the solution is best applied while heated to prevent precipitation of the urea.

When NaCl, KCl, ethanol and/or acetamide are present in DMSO-urea compositions, to effectively increase penetration or comfort, they should be present in a certain minimum amount. The combined weight of these agents, in ratio to the weight of urea present in the composition, should be greater than 1:99. Significant benefits are observed when the ratio is greater than 1:9.

The most effective formulations, at least for topical application, includes about six grams of urea, one gram of NaCl and at least six grams of water for every nineteen grams of DMSO. An aqueous medium is usually required for any DMSO-urea composition containing NaCl or KCl.

When included in DMSO compositions, urea, NaCl, and KCl may complex with DMSO molecules. As a result, such DMSO compositions may include DMSO-urea complexes, DMSO-salt complexes and/or DMSO-urea-salt complexes of various types. The exact effect that complexing has on the activity of the compositions containing DMSO and urea is not known. It is believed, however, that compositions containing the complexes listed above are effective in obtaining desirable reductions in side-effects and penetration increases When DMSO is used in the same composition with urea for the removal of cuticle, for treating diseased finger and toe nails, or for the remover of epidermal thickenings the composition should include a hydrophobic ointment base and at least 10 weight percent each of DMSO and urea to be effective. It is also advantageous to apply a salt such as NaCl or $Na_2S$. Use of such a salt increases the rate at which the nail or thickened skin are softened for removal. Specifically it appears that DMSO-urea compositions containing NaCl and/or $Na_2S$ penetrate more deeply into the area between the nail and plate than do compositions without such a salt component.

Such solutions for treating diseased nails should include between 0.25 and 10 weight percent of a salt selected from NaCl, $Na_2S$ and mixtures thereof, along with effective amounts of urea and DMSO. Less than 5 weight percent salt is found to be fully adequate in most instances.

To facilitate topical applications, any of the above compositions may include a pharmaceutically acceptable thickening agent to increase the viscosity of a composition. Such thickeners may be used to form creams, lotions, gels, pastes, ointments and suppositories.

Methods of Application

Urea may be administered with DMSO compositions by any route previously known for DMSO administration. The most dramatic reductions in side-effects are observed when urea is added to DMSO compositions for topical application. Subjects using topically applied DMSO suffer from substantially less malodorous breath, foul taste, and adverse skin reaction when urea is used along with the DMSO.

Topical applications of DMSO and urea may be by any standard technique. They may be painted or spread on and allowed to dry or applied with saturated pads. One advantageous method for treating limbs or digits is to place an appropriate DMSO-urea liquid composition in a plastic bag and insert the limb so that the bag forms an overwrap. Heat can be applied to the exterior of the bag to accelerate treatment.

Similary, spinal injuries can be treated by saturating a fabric with a DMSO-urea solution and then spreading the fabric along the spinal column. The fabric may be covered with a nonporous plastic sheet and hot water bottles applied to speed penetration of the DMSO-urea solution.

In most instances, it is preferred that DMSO and urea be combined in a common composition for administration together or otherwise be administered concurrently. In the specific case of topically applied DMSO composition, some reduction in side-effects is also observed if patients are treated with DMSO without urea after a preceeding treatment at the same site, with both DMSO and urea. For topical administrations at least, it is thus possible to use treatment regimens such as alternating applications of DMSO compositions with and without urea.

If a DMSO composition, for topical application, includes substances which would react adversely or be deactivated when combined with urea or would react with urea to form macromolecules which would retard tissue penetration, a urea composition can first be applied to the treatment site and allowed to dry. The DMSO composition could thereafter be applied at the same site with less chance that the urea-sensitive substances would be adversely affected. As desired NaCl, KCl, ethanol and/or acetamide can be included in the urea composition or, if compatible, in the DMSO composition.

As a penetration enhancing agent, urea can be administered with DMSO by topical administration, intravenous administration, subepidermal injection or oral ingestion. It can also be administered intrathecally, intravesically, rectally, or by instillation into eye, ear, nose or abnormal sinuses of the body.

The following examples describe a few of many clinical tests which show that the presence of urea can benefit pharmaceutical compositions containing DMSO. In each of the listed examples, DMSO and urea were applied in a common composition.

As previously mentioned, alternating applications of a DMSO composition and a urea composition may be advisable under some circumstances. For example, in the unusual circumstance that a preferrred DMSO composition contains a chemical agent that is unstable in the presence of urea, it would be preferable to alternate applications of the DMSO composition and a urea composition or to mix the two compositions immediately before administration. Sequential applications of DMSO and urea compositions or mixing immediately before application might also be preferred if the separate DMSO and urea compositions have a substantially longer shelf life than some combined formulation. Whether to combine urea with a particular DMSO composition is best determined by experimentation.

1. Cutaneous Administrations a. dermal administrations

EXAMPLE 1

|  | Wt. Percent |
| --- | --- |
| DMSO | 61.7 |
| water | 26.5 |
| urea | 8.8 |

-continued

|      | Wt. Percent |
|------|-------------|
| NaCl | 3.0         |

A control solution containing 62 wt. percent DMSO in water was also prepared. Both formulations were dermally applied to each of five human subjects known to be sensitive to compositions containing DMSO at a concentration of 50 wt. percent.

In a first test, the two solutions were topically applied concurrently but at different sites on skin of the subjects. Each subject complained of itching and burning at sites where the control solution was administered. And each had bad breath odor. At sites where the solution containing urea was applied, there was no discomfort or adverse skin reaction, even when the solution was applied to particularly sensitive areas of the neck, below the chin.

Several days later, the same subjects were treated with only the solution containing urea. There was no discomfort or adverse skin reaction. Neither bad breath nor foul taste were observed. Each of the subjects volunteered that their skin was softened when the compositions containing urea was applied.

After several more days, the subjects were again treated with the control solution. The subjects experienced a return of malodorous breath, foul taste, and adverse skin reactions.

EXAMPLE 2

A test was conducted to determine whether it would be advantageous to use DMSO compositions containing relatively large amounts of pharmaceutically acceptable agents having a weight per volume percentage concentration at isotonicity less than that of DMSO. Urea is such an agent. So, for comparison purposes, the composition of Example 1 was tested against the following composition which contains more urea and less water:

|      | Wt. Percent |
|------|-------------|
| DMSO | 61.7        |
| water | 17.6       |
| urea | 17.6        |
| NaCl | 3.0         |

Human subjects, suffering from a variety of ailments treatable with DMSO compositions, received each of the two formulations at separate times during the course of treatment. In every instance, the subject expressed a preference for the reformulated composition containing a greater amount of urea.

Specific benefits observed include prompter medicinal response and increased comfort (less tissue irritation). Effected skin area, of subjects suffering from scleroderma were softened when the high urea comcentration composition was applied topically. Such subjects receive no substantial relief when urea compositions without DMSO are applied.

EXAMPLE 3

The following composition was used to treat subjects suffering from contact dermatitis, from poison oak, insect bites and other conditions characterized by subdermal histamine release and consequent discomfort:

|      | Wt. Percent |
|------|-------------|
| DMSO | 47.6        |
| water | 33.3       |
| NaCl | 4.8         |
| urea | 14.3        |

Topical applications of this composition provided excellent results. Irritations and itching of the skin stopped promptly and were followed by rapid healing in all cases. Minor cuts were also treated with the above solution; and infection free healing resulted in each case.

EXAMPLE 4

DMSO compositions have been used successfully to treat a variety of athletic injuries such as sprains, muscle cramps, and the like. In this example, the following formulation was used:

| DMSO | 200 g. |
|------|--------|
| urea | 100 g. |
| ethanol (absolute) | 50 g. |
| water | 25 g. |
| methyl salicylate (as odorant) | 10 g. |
| 3% Carbopol 934 (carbomer-934) | 80 g. |
| triethanolamine | 2 g. |

Topical application of this composition has proved effective in test treatments for sprains, muscle cramps and other discomforts. Athletes receiving the above composition had no abnormal irritations.

One subject having very fair complexion and red hair was unable to tolerate a 50 wt. percent aqueous DMSO composition without urea. When a gel containing the above listed ingredients was applied to the skin of the subject, good medical relief was observed. Furthermore, there was no indication of the undesirable side-effects previously experienced from the application of DMSO without urea.

EXAMPLE 5

A methyl salicylate ointment was prepared for use for treating human subjects suffering from whiplash. The ointment included urea and ethanol to enhance penetration of methyl salicylate and DMSO. Specifically, it included:

| DMSO | 200 g. |
|------|--------|
| urea | 100 g. |
| water | 100 g. |
| ethanol | 50 g. |
| methyl salicylate | 10 g. |
| Carbopol 940 (carbomer-940) | 2.4 g. |
| triethanolamine | 2 g. |

This ointment was applied to the necks of whiplash victims who previously had experienced discomfort upon treatment with other DMSO substances. Methyl salicylate in the ointment penetrated extremely rapidly such that the subjects reported immediate relief from pain. The ointment was soothing when applied topically to low sensitivity skin areas and no malodorous breath or foul taste resulted.

EXAMPLE 6

The paste of Example 13 was used to impregnate polyolefin foam pads. The impregnated pads were applied to unpared calluses and corns on the foot of a subject. After daily treatments for four to eight days, the epidermal thickenings were sufficiently softened for easy removal.

EXAMPLE 7

Persons with more severe epidermal thickenings were treated according to the procedure of Example 13 using the composition of Example 6. Good success in the softening of tissue for removal was achieved.

EXAMPLE 8

The DMSO-urea composition of Example 1 was administered to patients suffering from a hardening of the skin as a result of incurable, progressive systemic sclerosis. Previously, these patients had each been treated for their condition with solutions of DMSO and water without urea, over a period of years.

After treatment with the DMSO-urea composition of Example 1, each of the patients reported a strong preference for that composition. Specifically, they reported relief from bad breath and a soothing effect upon application. Most significantly, skin of the subjects was softer and more flexible after several weeks of administration.

Also, blood circulation of the skin was improved. Systemic sclerosis typically impairs blood circulation to the skin as evidenced by a minimum of color change when finger pressure is applied to the effected area. After the patients were treated with the DMSO-urea composition of Example 1, once daily over the entire body for several weeks, vascular blanching of the skin was observed when finger pressure was applied. Blushing occurred upon release.

EXAMPLE 9

The vascular effect of DMSO compositions containing urea was observed in the dramatic recovery of one subject with ischemic ulceration of a finger. At the beginning of treatment, the finger was cyanotic, ulceration was progressing, and surgical amputation had been recommended.

In an attempt to improve this condition, the finger was treated by dipping in an aqueous DMSO solution. But the treatments were soon abandoned because the pain of treatment was too great.

In a second attempt at treatment, the finger was dipped in the following preparation over a period of several weeks:

|  | Wt. Percent |
| --- | --- |
| DMSO | 50 |
| water | 35 |
| urea | 10 |
| NaCl | 5 |

Twenty-five to fifty milligrams of indomethacin were added to each 500 grams of this solution to serve as an analgesic and anti-inflammatory agent.

After about 12 weeks of treatment, there was apparently full recovery of the finger with ulcer healing and excellent general appearance of the entire finger. At the end of the period amputation was counter-indicated; and treatment was stopped except for occasional applications to relieve discomfort.

EXAMPLE 10

DMSO and urea may be used effectively together, even at very low concentrations, when applied to animal membranes which have been stressed.

In one laboratory experiment hair was removed from both flanks of rabbits of about three kilogram body weight. The flanks were then blade shaved to fully expose the epidermis. Under anesthesia, the both flanks of five rabbits were severely scarified using a scalpel to expose subcutaneous tissues.

The right flank of each rabbit was kept continuously moistened with a 0.75 weight percent aqueous solution of DMSO containing 1.0 mg. of superoxide dismutase enzyme (m.w. 30,000-40,000) per 10 ml. of solution. The left flanks were treated identically except that the solution applied was free of DMSO.

It was observed that healing was greatly accelerated on the right flanks as compared to the left. Specifically, strong tension resistant healing of the right flanks occurred in about half the time.

The addition of urea to such low concentrated DMSO compositions can further improve healing rate, enhance enzyme penetration and eliminate side effects resulting from DMSO application. When applied to stressed tissue, not more than about 1.0 weight percent urea is required. For use in preparing the DMSO formulation of this example, it would be sufficient for the aqueous solution to contain about 0.75 weight percent urea.

EXAMPLE 11

Compositions containing methylsulfonylmetane (MSM) and urea improve the softness and pliability of skin even of persons suffering from adverse skin conditions. In one test, two human subjects suffering from "hide bound disease" or progressive systemic sclerosis were treated with a solution containing 20 weight percent MSM, 20 weight percent urea, 30 weight percent dimethyl sulfoxide and 30 weight percent water.

The subjects were treated by placing 15 milliliters of the solution in a plastic bag, placing a hand or foot to be treated in the bag. The hand or foot with plastic bag overwrap was then immersed in a heated water bath maintained at a temperature as warm as the subject would tolerate, taking care not to dilute the solution.

The hands and feet were thus immersed for 30 minutes, three times daily, for a period of two weeks. The result was a reduction in discomfort and increased skin softness and pliancy.

Dimethyl sulfoxide and urea in the solution enhanced penetration of MSM into the effected tissue. No adverse side-effects resulted from administration of the DMSO.

EXAMPLE 12

DMSO is a useful substance in many dermally applied cosmetic preparations. But, cosmetics containing DMSO are yet to be widely marketed because many test users experience malodorous breath and skin irritation. Such cosmetic preparations include the long-lasting antiperspirants described in U.S. Pat. No. 3,499,961.

To test whether such antiperspirants would be improved by the addition of urea, a comparison test was conducted.

A first paste was prepared containing, by weight, 10 parts of a 6:1 DMSO-aluminum chloride complex, 10 parts urea, 10 parts ethanol, 2 parts NaCl. Sufficient colloidal silica (Cab-O-Sil) was added to the other ingredients so that a proper paste consistency was achieved.

When applied to the left axilla of human subjects no breath odor or skin irritation resulted.

A second, similar paste was formulated without urea. This applied one hour later to the right axilla of the same subjects. The subjects experienced burning and itching of the right axilla within 15 minutes after application of the second paste. Malodorous breath was detected 30-35 minutes after application of the second paste.

EXAMPLE 13

An anti-mosquito lotion was prepared by combining the following ingredients, with heating, to form a solution:

| | |
|---|---|
| DMSO | 30 g. |
| ethanol | 30 g. |
| urea | 15 g. |
| N,N-diethyl-toluamide | 10 g. |

This preparation was applied to the skin of three human subjects, known to be sensitive to DMSO compositions. None of the subjects had adverse skin reactions, urticaria or bad breath odor.

b. nail administrations

EXAMPLE 14

A paste was prepared containing:

| | Wt. Percent |
|---|---|
| DMSO | 50 |
| urea | 40 |
| lanolin | 10 |

By heating the mixture to 60° and milled until a smooth, uniform paste was formed.

This paste was applied to a trauma injured toenail and underlying plate. After application, the toe was covered by a protective overwrap. At the seventh day after application, the nail was easily removed with gentle forcep urging.

EXAMPLE 15

Another paste was formed according to the composition:

| | Wt. Percent |
|---|---|
| DMSO | 45 |
| urea | 45 |
| NaCl | 5 |
| lanolin | 5 |

A mixture of these ingredients was heated to 60° C. and milled until a smooth, uniform paste was formed.

This paste was applied to a chronically defective fingernail of a human subject and also to a healthy nail on an adjacent finger. Both the fingers were covered by a protective overwrap. By the fifth day after application, the defective nail was easily removed by gentle urging with forceps. The normal nail was uneffected although cuticle of both fingernails was removable by gentle rubbing.

EXAMPLE 16

Another paste was formed having the composition:

| | Wt. Percent |
|---|---|
| DMSO | 45 |
| urea | 45 |
| sodium sulfide | 5 |
| lanolin | 5 |

This paste was prepared by heating to 60° C. amd milling to a smooth, uniform paste. This paste was applied to subjects having defective fingernails in the manner described in Example 15.

The paste of this example softened the defective nail and debrided the underlying nail plate more rapidly than did the paste of Example 15. A slight etching of the normal nail surface also occurred.

EXAMPLE 17

The following substances were mixed to form a gel:

| | |
|---|---|
| DMSO | 20 g. |
| urea | 40 g. |
| ethanol | 18 g. |
| water | 9 g. |
| isopropyl palmitate | 8 g. |
| Carbopol 940 (carbomer-940) | 2 g. |
| di(2-ethylhexyl)amine | 2 g. |
| griseofulvin | 1 g. |

Various subjects having defective fingernails with undergrowing fungal infection were treated using this gel composition. Gauze or polyolefin foam pads were impregnated with the gel, applied to the defective fingernails and covered by an occlusive overwrap. After 10 days, the overwrap and pads were removed. The diseased nails were then easily separated from the plate by forcep urging. After removal of the nail, a single painting of the preparation on the plate achieved both debridement of diseased and dead tissue and control of the infection.

EXAMPLE 18

In a related test, the composition of Example 16 was heated and then painted on diseased nails of human subjects. Twenty to thirty minutes after application, the nails were treated with an appropriate pharmaceutical composition, e.g. one containing an antimicrobial agent.

After several days of treatment, the diseased nail portions were removable by forcep urging and infections were under control.

EXAMPLE 19

Two liquid preparations were prepared for comparison purposes. These compositions were as follows:

| Preparation 1: | Wt. Percent |
|---|---|
| urea | 50 |
| water | 25 |
| DMSO | 25 |

The ingredients were mixed, heated to 50° C. and thereafter milled to a uniform dispersion.

| Preparation 2: | Wt. Percent |
|---|---|
| urea | 50 |
| water | 50 |

The ingredients were mixed, heated to 50° C. and thereafter stirred with cooling to form a uniform solution/dispersion.

Each of the preparations was used to impregnate cellulose base foam sheets. The sheets, in turn, were used to treat subjects having two adjacent digits with defective toe or fingernails. One digit of each subject was wrapped with a foam sheet containing Preparation 1 and the adjacent digit wrapped in a foam sheet containing Preparation 2. It was observed that Preparation 1 was about one-third more effective in softening defective, diseased nails for removal.

EXAMPLE 20

A nail conditioner was formulated from the following ingredients:

|  | Wt. Percent |
|---|---|
| water | 50 |
| dimethyl sulfoxide | 20 |
| methylsulfonylmethane (MSM) | 10 |
| urea | 10 |
| glycerine | 5 |
| glyoxal (30% aqueous) | 5 |

The formulation was applied with cotton pads to healthy nails of human subjects and allowed to remain for at least 15 minutes. At the end of that time, the nails were toughened, i.e. less brittle, and the cuticle was softened such that it could be removed by gentle rubbing.

It is not fully understood how the brittleness of the nail is reduced by application of the formulation. It appears, however, that the MSM is the principal active agent. The DMSO and urea appear to accelerate penetration of the MSM into the tough nail material.

Subjects using this formulation has no reddening or irritation of the skin surrounding the nail and did not suffer from malodorous breath.

2. Mucosal and Urogenital Administrations

EXAMPLE 21

The composition of Example 9 was slightly reformulated to include:

|  | Wt. Percent |
|---|---|
| DMSO | 50 |
| water | 35 |
| urea | 12 |
| NaCl | 3 |

This formulation was administered to patients suffering from urological problems such as prostatitis, through a catheter extending to the neck of the bladder. Clinical tests showed that patients receiving the DMSO-urea composition experienced significantly less discomfort and less malodorous breath than when a 50 wt. percent solution of DMSO in water was administered without urea. The DMSO-urea composition was equally effective in reducing the signs and symptoms of prostatitis.

EXAMPLE 22

The composition of Example 21 was administered to human subjects who suffered from interstitial cystitis, and who previously showed little improvement when treated with a 50 wt. percent solution of DMSO in water. In each case, thiry to one hundred milliliters of the composition was administered daily through a catheter inserted to the bladder.

As compared to treatment with the 50 wt. percent DMSO solution, the DMSO-urea formulation produced less patient discomfort. Also, improved therapeutic results were observed. Specifically, frequency of urination, pain and discomfort with bladder palpitation were reduced. Visual observation with a a cystoscope and biopsies of bladder tissue confirmed that there was a reduction in inflammatory lesions. After changing from treatment with aqueous DMSO to treatment with the DMSO-urea formulation, subjects' bad breath was significantly reduced.

EXAMPLE 23

For some time, DMSO has been used in concentrations of up to 100 percent for treating hypersensitive teeth recovering from extensive restorative oral surgery. Substantial pain and discomfort as well as trauma and localized tissue injury to the teeth and gums frequently results from such surgical procedures. DMSO is known to promote general tissue repair and reduce pain so that after about 2 weeks a patient can comfortably chew solid food again.

A young female subject recovering from oral surgery was treated with the following composition:

|  | Wt. Percent |
|---|---|
| DMSO | 71.4 |
| urea | 23.8 |
| water | 4.8 |

Cotton pledgets were saturated in the solution and applied to the gums. After two days of treatment both the relief of pain and the extent of healing were greater than observed for typical subjects receiving two weeks of treatment with high concentrations of DMSO solutions without urea.

Oral surgery patients treated with DMSO typically experience a sulfurous breath and bad aftertaste which can last for a full day after treatment. These adverse side-effects were greatly reduced in the subject treated with the above composition containing urea.

EXAMPLE 24

Another composition suitable for treating dental patients includes:

|  | Wt. Percent |
|---|---|
| DMSO | 70 |
| urea | 20 |
| water | 8 |
| NaCl | 2 |

When applied in the manner described in Example 23, this composition produces superior results in reducing dental pain and swelling associated with procedural trauma.

EXAMPLE 25

Elderly persons and subjects having connective tissue diseases, frequently have a problem with drying, painful gums. To treat this condition, the following composition was prepared:

| | |
|---|---|
| DMSO | 200 g. |
| urea | 50 g. |
| water | 50 g. |
| 3% Carbopol 934 (carbomer-934) | 10 g. |
| triethanolamine | 0.4 g. |

The Carbopol 934, a polymer of acrylic acid manufactured by B. F. Goodrich Chemical Co. of Cleveland, Ohio, in combination with triethanolamine as a neutralizer, caused the composition to be a soft gel. This was flavored with small amounts of spirits of peppermint to mask the somewhat bitter taste of DMSO.

When applied topically to the gums of subjects, pain was reduced and gum tissue was softened.

3. Intravenous Administrations

In current practice, DMSO is administered intravenously for a variety of therapeutic purposes, at a rate of 0.1 to 2.0 grams per kilogram body weight. Typically, intravenously administered DMSO is in an aqueous solution.

Subjects receiving DMSO intravenously have suffered from not only malodorous breath, but also from red blood cell lysis which could lead to renal failure. It is now found that urea, intravenously administered at the same time as DMSO, substantially reduces both red blood cell lysis and malodorous breath.

To effectively neutralize the hemolytic activity of DMSO and at the same time reduce expired dimethyl sulfide to acceptable levels, the amount of ethanol administered should be at least about 0.05 grams per kilogram body weight, up to about 0.5 grams ethanol per kilogram body weight. The ethanol should be administered in a weight ratio to DMSO of between about 1:40 and 5:1.

Superior results are achieved when the DMSO and urea are administered together in a common composition with the amount of urea being selected to be effective in reducing the undesirable side-effects of malodorous breath and/or hemolysis which can be expected from administration of the DMSO.

To enhance penetrating activity of DMSO administered intravenously, such solutions can contain substances to enhance penetration of the DMSO. Such substances include urea, NaCl, KCl and/or acetamide. In most instances, such solutions will contain water as a diluent.

Although several possible mechanisms can be postulated to explain the improvements resulting from intravenously administered ethanol, the actual mechanism whereby malodorous breath and red blood cell lysis are reduced, is not understood. The following examples illustrate the effectiveness of this treatment:

EXAMPLE 26

In a first test, nine volumes of whole, heparinized human blood were combined with one volume of a 50 volume percent aqueous solution of DMSO. The extent of red cell lysis was great and there was a pronounced evolution of dimethyl sulfide.

The test was repeated with the DMSO solution replaced by a 50 volume percent aqueous solution of ethanol. After the solution was combined with the blood, no odor was evolved but there was some red blood cell lysis.

In a third test, the procedure was repeated again, only the additive solution contained 66.6 volume percent DMSO and 33.3 volume percent ethanol. After one volume of solution was added to nine volumes of blood, neither red blood cell lysis nor dimethyl sulfide odor was observed. A sample of the atmosphere over the blood was collected and analyzed with a gas chromatograph. There was no detectable dimethyl sulfide peak.

EXAMPLE 27

Dog blood was drawn and heparinized to prevent clotting. After tubing, samples of the blood were mixed with a 20 wt. percent aqueous dimethyl sulfoxide solution in such an amount that the DMSO-blood mixture contained 12 grams of DMSO to every 100 g. of blood.

Upon mixing, there was almost instant red blood cell lysis with a predominant odor of dimethyl sulfide. The presence of dimethyl sulfide was confirmed by gas chromatography.

In a separate test, a sample of the heparinized blood from the same dog was combined with an aqueous solution containing 20 wt. percent DMSO and 10 wt. percent ethanol. The solution and blood were again combined so that 12 grams of DMSO were present for each 100 grams of blood in the resulting mixture. After mixing, only a small amount of red blood cell lysis occurred. The odor of dimethyl sulfide was absent, but gas chromatography analysis showed a small peak for dimethyl sulfide.

EXAMPLE 28

Two intravenous administration bottles were prepared. The first contained a 20 wt. percent aqueous DMSO solution. The second contained an aqueous solution having 20 wt. percent DMSO and 10 wt. percent ethanol. Two mongrel dogs of about 15 kg. body weight were catheterized. Then, the two solutions were delivered intravenously to the respective dogs so that each dog received 15 g. of DMSO (1 g. per kg. body weight).

When the first solution (DMSO-water) was administered to one dog, the laboratory rapidly filled with dimethyl sulfide odor. This odor was detected within 30-45 seconds after administration. Urine collected from the dog during the first hours after administration was a deep red color, indicating severe red blood cell lysis.

When the second solution was administered to the other dog, no dimethyl sulfide odor was detected by nose. Expired air from the animal was captured for a period of time in a toluene liquid trap. The trap was operated for 0.25 hours and the toluene was then analyzed by gas chromatography. There was a small peak showing that a trace of dimethyl sulfide had been collected.

Urine collected from the second dog was clean and on close observation was free of evidence of any red blood cell lysis. A unit of urine from the second dog was centrifuged and the sediment collected and observed. There were traces of a red precipitate, presumably hemoglobin. This may have been due in part to traumatization during catheterization or might represent a very slight amount of red blood cell lysis.

4. Hyperosmotic Administrations to Fish

As mentioned above, urea, NaCl, and acetamide may be beneficial in compositions for treating mammals. But, these same substances may be toxic to fish at concentrations of as little as 3 wt. percent in an aqueous solution applied to an epithelial membrane of the fish.

Because these substances are the driving force behind hyperosmotic treatment of fish, the toxicity places an upper limit on the extent to which hyperosmotic treatments can succeed.

It is now found that the lethality of certain solutions containing hyperosmotic concentrations of a membrane permeability altering agent can be reduced by adding DMSO to the composition. Such reformulated compositions can then be administered, in conjunction with health and/or welfare modifying agents, to an epithelial membrane, such as the gill membrane, of a water-living animal. The risk of death from osmotic stress is greatly reduced when the DMSO is used.

Suitable procedures for administration are described in U.S. Pat. No. 4,112,946. Other procedures for administration to epithelial membranes, particularly gill membrane, may also be used. A reduction in mortality rate will result in any instance where membranes is subjected to a composition having a moderately high hyperosmotic concentration of urea, NaCl and/or acetamide.

That DMSO would have this beneficial effect is quite surprising in view of the fact that DMSO is not greatly effective as a membrane permeability altering agent for treating the membranes of water living animals, particularly gilled animals.

Other dipolar, aprotic solutes, such as dimethyl acetamide (DMAC) and dimethyl formamide (DMF) are also beneficial in reducing mortality rate. But, these are less effective than DMSO.

The amount of dipolar, aprotic solute to use with a particular solution containing a hyperosmotic concentration of urea, NaCl and/or acetamide, is best determined by experimentation. The amount should be sufficient to produce a desired reduction in mortality rate or cell damage, but should not be so high as to expose the water-living animal subjects to toxic amounts of the solute. Also, if the solution includes a health and/or welfare modifying agent along with the permeability altering agent, the amount of the dipolar, aprotic substance administered should not be so great as to inhibit transport of the health and/or welfare modifying agent into the animals.

The following examples illustrate how DMSO is effective in reducing mortality due to osmotic stress.

EXAMPLE 29

A series of tests were made using twelve small goldfish (*Carassius auratus*). In each test, two fish were exposed, by imersion, to an aqueous test solution containing a hyperosmotic concentration of NaCl. The fish were exposed for five minutes each and thereafter were transferred to fresh water and observed. The results are summarized in Table I:

TABLE I

| Test | Solute | Conc. (wt. %) | Lethality |
|---|---|---|---|
| 1 | NaCl | 3 | 1 of 2 dead |
| 2 | NaCl | 4 | 2 of 2 dead |

TABLE I-continued

| Test | Solute | Conc. (wt. %) | Lethality |
|---|---|---|---|
| 3 | NaCl | 5 | 2 of 2 dead |
| 4 | NaCl | 3 | |
|   | DMSO | 3 | none |
| 5 | NaCl | 4 | |
|   | DMSO | 3 | none |
| 6 | NaCl | 5 | |
|   | DMSO | 3 | 1 of 2 dead |

Clearly, lethality was reduced when DMSO was used in combination with the NaCl.

It was also observed that the gills of all fish tested turned whitish upon exposure to the hyperosmotic solution. The degree of whiteness, a possible indicator of osmotic stress, corresponded to the concentration of NaCl. Less whiteness, at a given NaCl concentration, was observed in fish treated with the solutions containing DMSO.

EXAMPLE 30

The procedure of Example 29 was repeated, except that after exposure to the hyperosmotic solutions, the goldfish were transfered to fresh water containing 0.5 wt. % trypan blue dye. The results appear in Table II:

TABLE II

| Test | Solute | Conc. (wt. %) | Lethality |
|---|---|---|---|
| 7 | NaCl | 3 | none |
| 8 | NaCl | 4 | 2 of 2 dead |
| 9 | NaCl | 5 | 2 of 2 dead |
| 10 | NaCl | 3 | |
|    | DMSO | 3 | none |
| 11 | NaCl | 4 | |
|    | DMSO | 3 | none |
| 12 | NaCl | 5 | |
|    | DMSO | 3 | none |
| 13 | urea | 8 | none |
| 14 | urea | 12 | none |
| 15 | urea | 8 | |
|    | DMSO | 5 | none |
| 16 | urea | 12 | |
|    | DMSO | 5 | none |

Again, decreased lethality was observed for fish exposed to a NaCl solution, when DMSO was added.

The fish were observed for dye uptake. Trypan blue, being a vital exclusion type dye, only colors non-living cells. Fish exposed to the saline solutions without DMSO demonstrated an increased dye uptake, pronounced when the NaCl concentration was 5 wt. percent. From the dye uptake patterns observed, it appears that NaCl without DMSO is highly lethal to epithelial cells, especially of the gills, fins and tail.

Similar results were observed in tests 13-16 where the fish were exposed to hyperosmotic concentrations of urea. Although none of the test animals died, dye uptake was greater when DMSO was absent.

These results are contrary to expectations because DMSO is known to facilitate tissue penetration in most instances. If DMSO behaved in an expected manner, it would enhance NaCl and urea penetration. Such increased penetration should logically increase cell damage and, consequently, trypan blue uptake. But, the results of tests 7-16 show that the opposite is true. DMSO protects cells from attack by hyperosmotic NaCl and urea solutions, and does not aid in the attack. Furthermore, the results of tests 7-16 indicate that DMSO not only reduces the lethality of hypersomotic solutions, but also retards injury of cells exposed to extreme osmotic challenge.

EXAMPLE 31

Seven fingerling salmonids of 4-5 inch length were netted in the Washougal River (State of Washington). The species was not identified; but most likely the fingerlings were wild, coho salmon (Oncorhynchus kisutch).

Four of the fingerlings were immersed in an aqueous solution containing 5 wt. percent NaCl and 3 wt. percent DMSO. After five minutes, the fingerlings were returned, for observation, to a holding pond containing river water. The procedure was repeated with the remaining three fingerlings being immersed in an aqueous solution containing only 5 wt. percent NaCl.

All of the fingerlings lost their friskiness when exposed to a hyperosmotic solution, but all were alive when transferred to the holding ponds. After three hours, the three fingerlings exposed to the NaCl solution without DMSO had died. The other four fingerlings were alive and were released into the river.

While I have described and given examples of preferred embodiments of my invention, it will be apparent to those skilled in the art that changes and modifications may be made without departing from my invention in its broader aspects. I therefore intend the appended claims to cover all such changes and modifications as fall within the true spirit and scope of my invention.

I claim:

1. In a method for administrating dimethyl sulfoxide to a host, the improvement comprising reducing the side effects of malodorous breath and skin reactions normally associated with such dimethyl sulfoxide administration, comprising the step of:

administrating to said host a composition comprising dimethyl sulfoxide and a side-effect reducing agent taken from the group consisting of urea, or ethanol or mixtures thereof in an amount which is effective for said purpose.

2. A method according to claim 1 wherein said composition further includes acetamide.

3. The method according to claim 1 wherein said composition further includes sodium chloride.

4. The method according to claim 1 wherein said composition further includes potassium chloride.

5. The method according to claim 1 wherein said composition further includes water.

6. The method according to claim 1 wherein the weight ratio of urea to dimethyl sulfoxide is greater than 1:99.

7. The method according to claim 1 wherein the ratio of urea to dimethyl sulfoxide is greater than 1:9.

8. The method according to claim 1 wherein said composition has the following formulation:

| | |
|---|---|
| dimethyl sulfoxide | about 19 grams; |
| urea | about 9 grams; |
| sodium chloride | about 1 gram; and |
| water | at least about 6 grams; | whereby the aforementioned composition formulation is provided with the weight ratios noted.

* * * * *